United States Patent [19]

Stevens et al.

[11] Patent Number: 6,034,246
[45] Date of Patent: *Mar. 7, 2000

[54] 2-ARYLBENZAZOLE COMPOUNDS

[75] Inventors: Malcolm Francis Graham Stevens, Leicestershire, United Kingdom; Dong-Fang Shi, Texas, Tex.; Tracey Dawn Bradshaw; Samantha Wrigley, both of Nottingham, United Kingdom

[73] Assignee: Cancer Research Campaign Technology Limited, London, United Kingdom

[ * ] Notice: This patent is subject to a terminal disclaimer.

[21] Appl. No.: 08/919,206

[22] Filed: Aug. 28, 1997

Related U.S. Application Data

[63] Continuation of application No. PCT/GB96/00440, Feb. 28, 1996.

[30] Foreign Application Priority Data

Feb. 28, 1995 [GB] United Kingdom .................. 9503946

[51] Int. Cl.[7] ...................... C07D 277/66; C07D 263/57; A61K 31/425; A61K 31/42
[52] U.S. Cl. .......................... 548/152; 514/321; 514/367; 514/375; 546/198; 548/178; 548/179; 548/180; 548/217; 548/233.8; 424/400; 424/464; 424/489; 424/451
[58] Field of Search .................................... 548/152, 180, 548/217, 233.8, 178, 179; 546/198; 514/367, 375, 321

[56] References Cited

U.S. PATENT DOCUMENTS

| | | | |
|---|---|---|---|
| 2,780,628 | 2/1957 | Porter | 548/152 |
| 3,279,918 | 10/1966 | Cassiers et al. | 548/152 X |
| 5,371,232 | 12/1994 | Bomba et al. | 548/152 |
| 5,496,826 | 3/1996 | Watson et al. | 514/303 |
| 5,874,431 | 2/1999 | Stevens et al. | 514/233.8 |

FOREIGN PATENT DOCUMENTS

| | | |
|---|---|---|
| 3141430 | 5/1983 | Germany . |
| 3307364 | 9/1984 | Germany . |
| 4-327581 | 11/1992 | Japan . |

OTHER PUBLICATIONS

Guellue et al, Bull. Soc. Chim. Belg., vol. 103(3), pp. 87 to 90, 1994.

Kanaoka et al, Chem. Pharm. Bull., vol. 18(3), pp. 587 to 590, 1970.

Rao et al, Indian J. Pharm. Sci., vol. 51(5), pp. 192 to 194, 1989.

Wolfbeis et al, Monatsh, Chem., vol. 114(5), pp 599 to 604, 1983.

*Primary Examiner*—Floyd D. Higel
*Attorney, Agent, or Firm*—Pillsbury Madison & Sutro LLP

[57] ABSTRACT

There are disclosed herein 2-phenylbenzazole compounds having a 3'-substituent and a 4'-$NR^2R^6$ substituent in the phenyl group where $R^5$ and $R^6$ are each hydrogen or alkyl, or where the $'-NR^5R^6$ substituent is N-acyl (or N-benzoyl). There are also disclosed 2-phenylbenzazole compounds in the form of 4'-N sulphamate salts. Such compounds exhibit significant selective cytotoxic activity in respect of tumor cells and provide potentially useful chemotherapeutic agents for selective treatment of a range of cancers.

24 Claims, 2 Drawing Sheets

FIG. 1

FIG. 2

ROUTE A

ROUTE B

ROUTE C

ROUTE D

ROUTE E

2-ARYLBENZAZOLE COMPOUNDS

This application is a continuation of PCT/GB96/00440 filed Feb. 28, 1996.

FIELD OF THE INVENTION

The present invention relates to certain novel benzazole compounds, specifically 2-arylbenzazole compounds, and compositions thereof which are biologically active in that they are able selectively to inhibit proliferation of certain mammalian tumor cells.

BACKGROUND AND SUMMARY OF THE INVENTION

Various 2-arylbenzazole compounds found to be active in inhibiting proliferation of certain tumor cells and exemplified by 2-(4'-aminophenyl) benzothiazole and close analogues or acid addition salts thereof are disclosed in PCT international patent application No. PCT/GB94/01883 published Mar. 9, 1995 under No. WO 95/06469.

The compounds with which the present invention is concerned are also 2-arylbenzazole compounds which are believed to comprise novel or new chemical entities and which are of particular interest as active chemotherapeutic agents for use in therapy, especially antitumor therapy, by virtue of an ability to inhibit proliferation of certain tumor cells.

For some of the benzazole compounds disclosed in the aforesaid PCT international patent application, for instance the compound 2-(4'-aminophenyl) benzothiazole which has been designated the reference code CJM 126, a remarkably high specific inhibitory activity has been found in respect of certain human breast cancer cell lines. It has now also been found, however, that some of the compounds previously disclosed in said prior PCT application, and benzazole compounds newly disclosed in the present application, can exhibit anti-proliferative activity selectively in respect of a number of different cell lines that relate to a range of various mammalian cancers other than human breast cancer. The present invention accordingly envisages the use of 2-arylbenzazole compounds as specified for making medicaments or pharmaceutical compositions for use in antitumor therapy not necessarily only for the treatment of breast cancer but additionally, or alternatively, for the treatment of certain other selected cancers.

More specifically, the benzazole compounds of the present invention are generally 2-arylbenzazole compounds represented by the structural formula I below, or a pharmaceutically acceptable salt thereof,

I characterised in that

X is S or O;

$R^1$ and $R^3$ are each independently hydrogen, alkyl, hydroxyl, alkoxy, or aralkoxy;

$R^2$ is selected from hydrogen, $NO_2$, $NH_2$, halogen, alkyl, CN, and a substituted alkyl oxysulphonyl group;

$R^5$ and $R^6$ are each independently hydrogen, alkyl, or an acyl or benzoyl group where Y is O or S, and $R^8$ is alkyl (including cyclo-alkyl), a halogenated lower alkyl, or phenyl, or $SO_3^-M^+$ where $M^+$ is a monovalent cation or cationic group, and $R^7$ is hydrogen, 5'-halogen or 5'-alkyl subject to the following provisos:

(a) when $R^5$ and $R^6$ are each hydrogen or alkyl, $R^2$ is not hydrogen but is a 3'-substituent in the phenyl group other than a 3'-substituted alkyl oxysulphonyl group;

(b) $R^7$ is limited to being hydrogen unless $R^2$ is a 3'-substituent in the phenyl group;

(c) if $R^2$ is $NO_2$ it is a 3'-substituent in the phenyl group;

(d) alkyl groups when present as such in the compound or as a moiety in other groups such as alkoxy are each composed of less than 6 carbon atoms;

(e) the compound is not 2-(4'-amino-3'-iodophenyl) benzothiazole (unless in the form of a sulphamate salt thereof).

Preferred compounds of the invention in accordance with formula I wherein $R^3$ is hydrogen include compounds in which $R^1$ is alkyl, alkoxy or benzyloxy. It is also usually preferred that X be sulfur. Preferred compounds of the invention in accordance with the structural formula I may also be further characterised by at least one of the following features:

(a) at least some alkyl groups when present as such or as a moiety in other groups such as alkoxy are methyl or ethyl;

(b) halogen substituents, when present, are selected from iodine, bromine and chlorine.

It has been found that at least for compounds of structural formula I wherein $R^5$ and $R^6$ are both hydrogen, i.e. wherein the phenyl group has a 4'—$NH_2$ substituent, a very effective degree of anti-proliferative activity against various mammalian tumor cells may arise when $R^2$ is a halogen atom, or is a lower alkyl group (preferably Me or Et), in the 3' position of the phenyl group. For example, the particular combinations of 4'—$NH_2$ and 3'—Cl, 4'—$NH_2$ and 3'—Br, 4'—$NH_2$ and 3'—I, 4'—$NH_2$ and 3'—Me, and 4'—$NH_2$ and 3'—Et in the phenyl group of the 2-aryl component have been found to yield compounds with potent anti-proliferative properties against at least some selected tumor cells. The 3' position substituent may alternatively be a cyano group, giving a further combination 4'-$NH_2$ and 3'—CN.

In these compounds in which $R^2$ is a 3'-substituent in the phenyl group, when $R^1$ is an alkyl, alkoxy or benzyloxy substituent it is generally preferred that $R^1$ should be a substituent in the 6-position of the benzazole moiety.

Compounds in accordance with the invention which conform to formula I wherein $R^2$ is a 3'-substituent in the phenyl group, and which are of particular interest, include those compounds where $R^5$ and $R^6$ are both hydrogen and the combination of substituents $R^1$, $R^2$, $R^3$, $R^7$ and X is selected from the following combinations:

| R¹ | R³ | X | R² | R⁷ | Ref. No. |
|---|---|---|---|---|---|
| H | H | S | 3'-Me | H | (DF203) |
| H | H | S | 3'-Et | H | (DF223) |
| 6-Me | H | S | 3'-I | H | (DF219) |
| 6-OMe | H | S | 3'-I | H | (DF210) |
| H | H | O | 3'-1 | H | (DF206) |
| H | H | S | 3'-Br | H | (DF209) |
| 6-Me | H | S | 3'-Br | H | (DF220) |
| H | H | S | 3'-Cl | H | (DF229) |
| H | H | S | 3'-CN | H | (DF230) |
| H | H | S | 3'-Br | 5'-Br | (126) |
| H | H | S | 3'-Cl | 3'-Cl | |
| H | H | S | 3'-Cl | 5'-Me | |

Another group of benzazole compounds which provide some very promising anti-proliferative agents for use in antitumor therapy are compounds conforming to structural formula I wherein the substituent NR⁵R⁶ is an N-acyl or N-diacyl derivative) or equivalent benzoyl derivative) e.g.

where, as hereinbefore specified, Y is O or S and R⁸ is a lower alkyl (including a cyclised lower alkly such as cyclobutyl), or a halogenated lower alkyl, or phenyl.

Acyl or benzoyl derivatives as referred to above which are of particular interest include those compounds where NR⁵R⁶ is an N-acyl group (or N-benzoyl group) and where the combination of substituents R¹, R², R³, R⁸, X and Y is selected from the following combinations.

| R¹ | R³ | X | R² | Y | R⁸ | Ref. No. |
|---|---|---|---|---|---|---|
| H | H | S | H | O | Me | (DF128) |
| H | H | O | H | O | Me | (DF140a) |
| H | H | S | H | S | Me | (DF188) |
| H | H | O | H | S | Me | (DF175) |
| H | H | S | H | O | CH₂Cl | (DF180) |
| H | H | O | H | O | CH₂Cl | (DF190) |
| H | H | O | 3'-I | O | CH₂Cl | (DF225) |
| H | H | O | 3'-NO₂ | O | Me | (DF214) |
| H | H | S | H | O | CHCl₂ | (DF232) |
| H | H | S | H | O | Ph | (DF131) |
| H | H | S | H | O | Cyclobutyl | (KF497) |

Reference code numbers are denoted in brackets for some of the above compounds for which more detailed preparative examples are hereinafter presented.

It will also be understood that many of the compounds in accordance with the invention which are herein referred to may be presented in the form of pharmaceutically acceptable salts, especially acid addition salts derived from an acid selected for example from the group comprising: hydrochloric, hydrobromic, sulphuric, nitric, phosphoric, maleic, salicyclic, p-toluenesulphonic, tartaric, citric, lactobionic, formic, malonic, pantothenic, succinic, naphthalene-2-sulphonic, benzene-sulphonic, methanesulphonic and ethanesulphonic.

It should also be understood, however, that where reference is made in this specification to compounds of formula I such reference should be construed as extending not only to their pharmaceutically acceptable salts but also to other pharmaceutically accepatble bioprecursors (pro-drug forms) where relevant. Moreover, where any of the compounds referred to can exist in more than one enantiomeric form, all such forms, mixtures thereof, and their preperation and uses are within the scope of the invention.

More particularly, sulphamate salts consititing potential water-soluble pro-drug forms of the 2-(aminophenyl) benzazole compounds previously mentioned, especially para amino or 4'—NH₂ derivatives, provide a further category of promising benzazole compounds within the scope of the present invention. These sulphamate salts may break down in biological systems to form corresponding amines, and will generally be compounds conforming to structure I wherein NR⁵R⁶ is 4—NHSO₃⁻M⁺ as hereinbefore defined. In preferred embodiments M⁺ is an alkali metal cation such as Na⁺ or is a cationic group such as NH₄⁺.

Like acyl derivatives such as N-acetyl and N-chloroacetyl derivatives, and like other acid addition salts, e.g. hydrochloride, dihydrochloride, methanesulphonic acid and ethanesulphonic acid addition salts, these sulphamate salts are expected to be equally effective in inhibiting proliferation of tumor cells in antitumor therapy as the parent amino compounds from which they may be considered to be derived. The salts may of course dissociate in water or other aqueous media to provide the active antitumor compound, and in practice these water soluble compounds are likely to be the most preferred compounds for making up acceptable pharmaceutical formulations. It may for example be noted that the sulphamate salt hereinafter described and designated by the reference code DF183 has been found to have an aqueous solubility of about 10 mg/ml whereas that of the compound 2-(4'-aminophenyl) benzolthazole referred to as CJM 126 has an aqueous solubility of only 3.8 μg/ml.

Specific sulphamate salts in accordance with formula I which are of particular interest include compounds in which the combination of substituents R¹, R², R³, NR⁵R⁶ and X is selected from the following combinations:

| R¹ | R³ | X | R² | NR⁵R⁶ | Ref. No. |
|---|---|---|---|---|---|
| H | H | S | H | NHSO₃⁻Na⁺ | DF183 |
| H | H | S | H | NHSO₃⁻NH₄⁺ | DF191 |
| H | H | O | H | NHSO₃⁻Na⁺ | DF187 |
| H | H | S | 3-I | NHSO₃⁻Na⁺ | DF224 |
| H | H | S | 3-Me | NHSO₃⁻Na⁺ | DF228 |

The invention also comprises the use of a 2-arylbenzazole compound as specified above for therapy, especially for making a medicament or pharmaceutical composition for selective use in antitumor therapy.

As hereinafter described, the invention also includes pharmaceutical compositions or preparations, conveniently in unit dosage form, for selective use in antitumor therapy, said compositions or preparations comprising as the active substance a 2-arylbenzazole compound as herein specified.

Biological Activity

In Vitro Activity

Tables 1 to 4 at the end of the present description show in vitro test results obtained in various sets of experiments for the cytotoxic activity of several of the benzazole compounds concerned, including also for reference results for the compound CJM 126 and comparative results for compound DF129, when tested against a range of tumor cell lines which includes ovarian, lung and certain colon and renal cancer cells from the National Cancer Institute (USA) collection. As usual the results are expressed in terms of $IS_{50}$ values (concentration or dosage required to reduce cell growth or proliferation by 50%) calculated from dose-effect curves plotted for cultures of the cells in question.

It will be seen in Table 1 that the lung cancer cell lines referred to therein were not very sensitive to CJM 126, but other benzazole compounds listed had a relatively high activity against certain of these lung cancer cell lines. Particularly notable is the activity of DF129 and DF203 against the MOR/P (parental line), MOR/R (multidrug resistant line) and MOR/CPR (cisplatin resistant line) since it is most unusual for a compound to be more active against the MOR/CPR line than against the two other lines. This effect in fact suggests that these compounds have a general property of useful action against platinum-resistant tumors.

Similarly, Tables 2, 3 and 4 show a relatively high inhibitory activity of some benzazole compounds identified therein against at least certain ovarian, colon and renal cancer cell lines as well as against human breast tumor cell lines. Again, the increased activity of compounds DF129 and DF203 against the platinum-resistant ovarian cancer cell subline A2780-cisR compared to the parental line A2780 is notable, but it will be seen that in respect of the ovarian cancer cell lines compound DF 180 was the most active by far and, interestingly, was substantially equiactive against two cisplatin resistant cell lines as the parental line.

It is also of particular interest to note that compounds DF129, DF209 DF203, wherein the 2-(4'-aminophenyl) fragment contains respectively 3'—I, 3'—Br and 3'—Me substituents, are more potent than even the compound CJM 126 against the breast cancer cells tested (see Table 4). Also, it will be seen that even the chloroacetyl derivative DF180 shows a useful degree of inhibitory activity in respect of these breast cancer cell lines.

Overall, these results clearly demonstrate strong characteristics of selective inhibition.

In carrying out the in vitro studies, the cytotoxicity assays may be carried out by a method corresponding substantially to the following example:

Cells were maintained in a continuous logarithmic culture in Dublecco's medium supplemented with 10% fetal calf serum and penicillin (100 IU/ml) and streptomycin (100 $\mu$m). The cells were mildly trypsinized for passage and for use in assays. On day zero, 100 $\mu$l of trypsinized tumor cells ($1 \times 10^4$/ml) were plated in the wells of 96-well flat-bottom microtiter plates. The plates were incubated for 2 days at 37° C. and 5% $CO_2$ in air to allow the cells to adhere and resume exponential growth prior to the addition of drugs.

The components being tested were dissolved in a small volume of DMSO and diluted to the desired concentration with growth medium so that the final concentration of DMSO did not exceed 0.25%. On day two 50 $\mu$l of the highest drug concentration was added to the wells of column 12 and from there serially diluted 3-fold to column 1 by serial transfer of 50 $\mu$l using an 8-channel micropipette. The final volume of column 1 was adjusted to 100 $\mu$l. No additions were made to the wells of rows A and B, which served as controls. The plates were further incubated for 5 days at 37° C. and 5% $CO_2$ in air. Each compound was tested in duplicate.

On day 7 the test was terminated by the addition of 100 $\mu$l saline containing 0.002% w/v propidium iodide (Sigma), 0.3% drawing ink (Staedtler "Marsmatic 745"—Trade Mark) and 0.5% Triton X-100. The plates were kept at 4° C. overnight before reading on an inverted microscope equipped with an automated scanning stage. Fluorescence intensity was measured in arbitrary units by a photomultiplier. An HP-87 computer controlled the movement of the stage and also collected and processed the data from the multiplier.

For each compound tested a dose-response curve was obtained and the $IC_{50}$ value (the drug concentration at 50% inhibition of cell growth) was calculated.

Agent Cytotoxicity

This was estimated by measuring the leakage of lactate dehydrogenase (LDH) from cells damaged by toxin insult. Cells were seed into 24-well plates in medium supplemented with 1% FCS at a density of $5 \times 10^4$/well and allowed 4 hours to attach before drug was administered (final concentration 1 nm-100 $\mu$M, n=3/control n=6). Following 96 hours exposure, medium was collected, centrifuged to pellet any debris and assayed for LDH activity. Concurrently, cells were counted using a haemocytometer. The oxidation of NADH to $AND^+$ by LDH was measured spectrophotometrically by following the decrease in absorption at 340 nm. 2.4 ml PBS, pH 7.4, 0.1 ml NADH (3.5 $\mu$M) and 0.4 ml medium sample were added to a cuvette. The assay mixture was allowed to equilibrate at 37° C. before initiating the reaction by addition of 0.1 ml sodium pyruvate solution (32 $\mu$M). The rate of change of absorbance over 5 minutes was monitored on a Pye Unicam SP8-400 UV/VIS spectrophotometer. Maximal release of LDH, representing 100% cell death, was determined following lysis of untreated cells in 1% Triton-X 100 (Redg. Trade Mark). LDH release was measured in untreated cells to obtain a value representing natural cell death. Agent cytotoxicity was expressed as % Triton-releasable LDH activity/$10^5$ cells, and the drug concentration which elicited 50% toxicity ($LD_{50}$ value) was calculated.

In Vivo Antitumor Tests

Some of the compounds have also been subjected to in vivo tests. In general, the results in these in vivo tests have reflected the results in corresponding in vitro tests, and the present indications are that the benzazole compounds herein disclosed will provide useful antitumor agents for selective use in medicine.

In one typical set of experiments, four human breast carcinomas xenotransplanted into female Ncr: nu/nu (Taconic, Germantown, U.S.A.) or male Bom: NMRI-nu/nu mice (Bomholtgaard, Ry, Denmark) were used for the evaluation of antitumor activity. Mice weighing 20–25 g at the start of experiments were held under sterile conditions at 24–26° C., 50% relative humidity and 12 hours light-dark rhythm in laminar flow shelves. The animals received autoclaved food and bedding; the drinking water was filtered and acidified (pH4.0).

The following breast carcinoma cell lines were used: BO; MCF-7 (NCI, U.S.A.); MT-1 and MT-3. The tumors BO and MCF-7 are $ER^+$ models: the carcinomas MT-1 and MT-3 are $ER^-$ ones. Tumors were transplanted subcutaneously (s.c.) as pieces (2×2 mm) into the left flank of 5–8 nude mice/experimental group. Drug treatment was initiated when the tumors reached a diameter of 4–5 mm. Compounds were solubized with Tween 80 (maximum 10% of final volume) and suspended in saline. Suspensions were preparated freshly for each drug administration and injected in a volume of 0.2 mL/20 g body weight employing a once-weekly schedule (x3). Tumor size was measured twice weekly with a caliper. Median tumor volume/group was related to the first treatment day and expressed as Relative Tumor Volume (RTV). For the estimation of toxicity, body weight was determined twice weekly and the mean percentage body weight change (BCC) was calculated. In one experiment blood was obtained from the retroorbital venous plexus of mice and blood cells were determined with a Coulter counter (Model T41).

Figure 1:
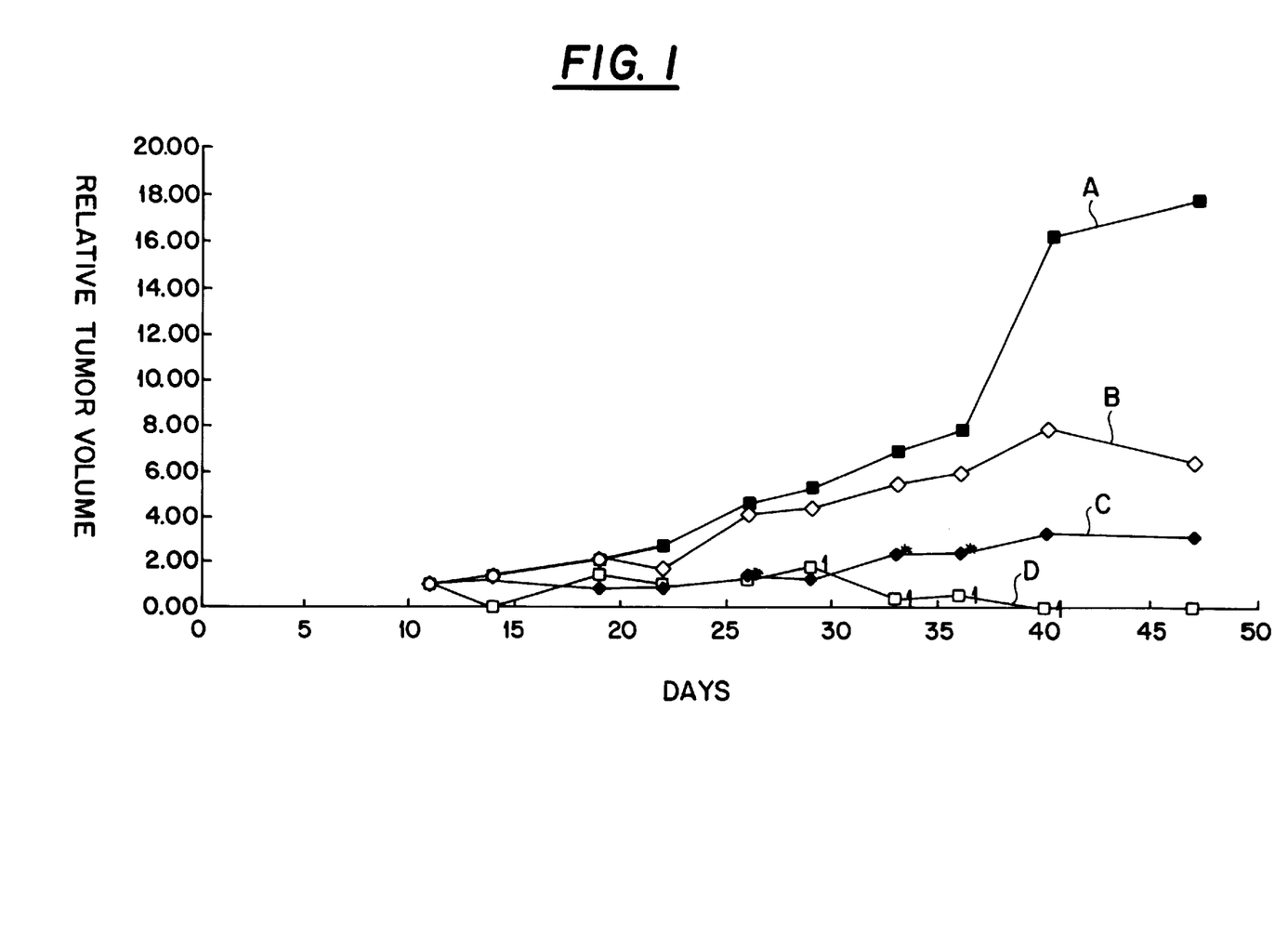

Some of the in vivo test results are shown in Tables 5 and 6 at the end of the present description, and in FIG. 1 of the accompanying drawing which illustrates the results for measurements of in vivo activity of 2-(4'-amino-3'-methylphenyl) benzothiazole (DF203) against MCF7 in nude mice administered on days 12, 19 and 26. In FIG. 1:

Curve A represents a saline control;
Curve B shows the results for a dose of 6.25 mg/Kg administered by injection;
Curve C shows the results for a dose of 12.5 mg/Kg administered by injection;
Curve D shows the results for a dose of 25 mg/Kg administered by injection.

As a preliminary to the in vivo tests the maximum tolerated doses (MTDs) of four test compounds administered as single doses (i.p.) in female BDF1 mice were assessed. Both compound CJM 126 and the 2-(3-aminophenyl) isomer included for reference purposes elicited inhibitory effects against the breast carcinoma BO as shown in Table 5, although it is of interest to note that in the former case the influence on both tumor growth and body weight was relatively independent of dose.

The in vivo activity of the amines DF203 and DF129 in a panel of four or two, respectively, xenotransplanted breast carcinomas is recorded in Table 6. Whereas compound DF129 displayed only borderline activity in one of the models, compound DF203 induced a consistent tumor growth inhibition in all four tumors. The results of one representative test against the MCF-7 carcinoma are shown in FIG. 1. Although compound DF203 was found to be toxic at the top dose of 25 mg/Kg with only one survivor, the surviving animal was tumor free and no overall change in white blood cell or platelet counts were measured, indicating that bone marrow toxicity is not dose-limiting. The activity of compound DF203 against the ER-tumors MT-1 and MT-3 was also notable because these tumors are predictive for the clinical activity of cyclophosphamide, adriamycin and mitoxantrone and are exquisitively sensitive to hexadecylphosphocholine and other ether lipids. In contrast these tumors are completely unresponsive to methotrexate and vincristine, and only modestly sensitive to cisplatin.

At present, the pharmacological mechanism responsible for the unusual activity of this new series of compounds is unknown.

Preparative Methods

Figure 2:
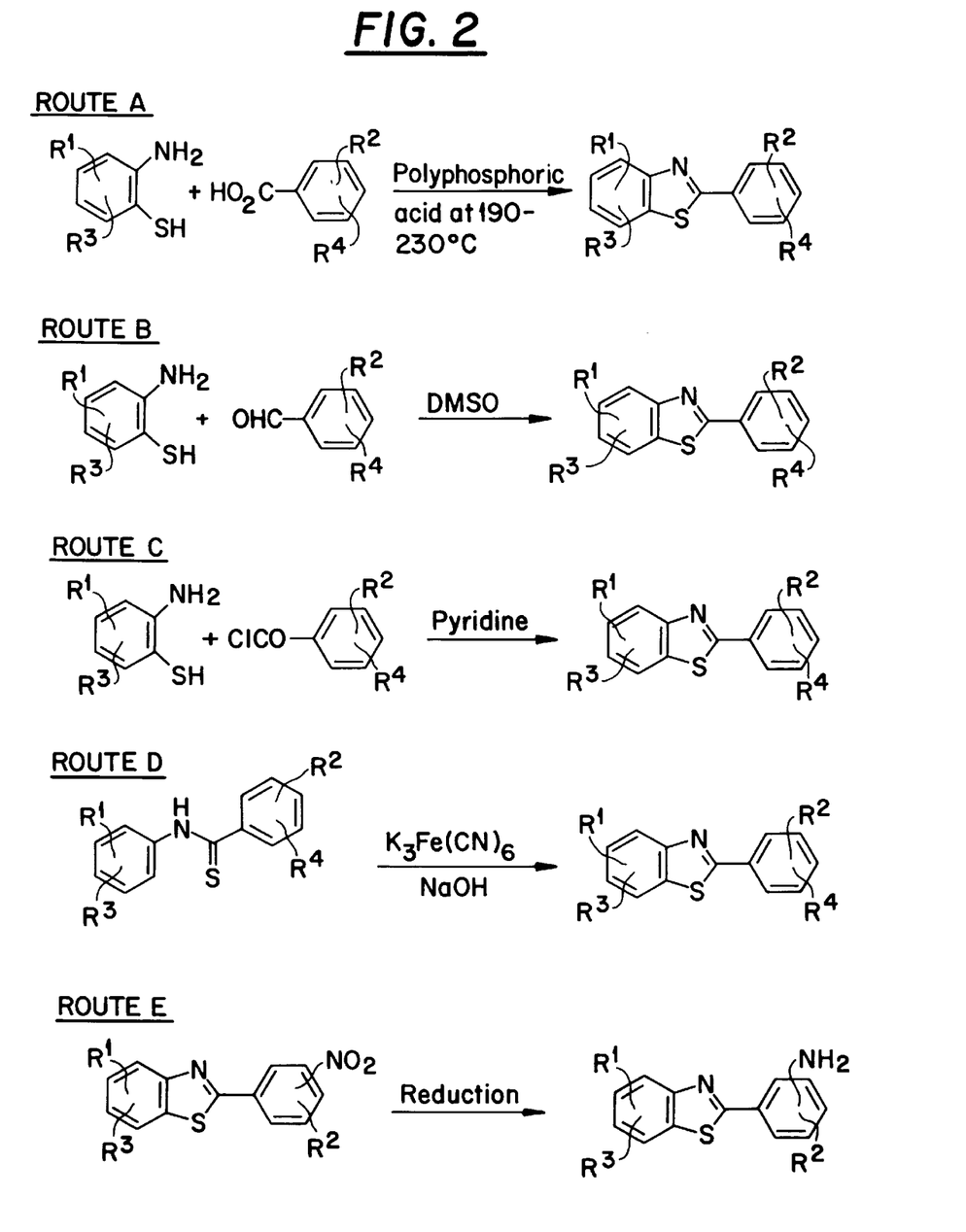

In most cases the 2-arylbenzazole compounds of the present invention can readily be synthesised by various routes from easily available starting materials, and by way of example, several such general synthetic routes, designated Route A, Route B, Route C, and Route D, are illustrated in FIG. 2 of the accompanying drawings in relation specifically to 2-arylbenzothiazole compounds. A reduction scheme for converting a nitro substituent of an arylbenzothiazole compound into an amino substituent is also depicted as Route E. Such nitro compounds are often conveniently prepared for use as intermediates in producing the corresponding amino compounds.

In the general method for Route A, which is also applicable to the synthesis of corresponding benzoxazole compounds, typically a mixture of the 2-aminothiophenol (0.05 Mol.), or 2-aminophenol for a benzoxazole, and the appropriate benzoic acid derivative (0.05 Mol.), together with polyphosphoric acid (85 g), is heated at 190–230° C. for 4 hours, cooled and poured into a mixture of 10% aqueous sodium bicarbonate (1000 ml) and ice. The solid product may then be collected, washed with water and recrystallized.

With this method, in some cases the benzoic acid derivative may be replaced by a corresponding substituted benzonitrile.

In the general method for Route B, typically a mixture of 2-aminothiophenol (0.05 Mol.), the appropriate benzaldehyde (0.05 Mol.) and dimethylsulphoxide (30 ml) is heated to 180° C. for 15 minutes, cooled and diluted with water (200 ml). The precipitate is then collected, washed with water and crystallised.

In the general method for Route C, assuming for example that $R^2$ is a nitro group $NO_2$, a solution of the 2-aminothiophenol (0.05 Mol.) in pyridine (50 ml) is added slowly to a mixture of the appropriate nitrobenzoyl chloride (0.05 Mol.) also in pyridine (50 ml) at 25° C. The reaction is exothermic and is cooled in an ice-beth. The mixture may then be diluted with water (200 ) and the products are collected and washed with water.

In the general method for Route D, in a typical procedure the appropriate substituted thiobenzanilide (1 Mol. equiv.) is finely powdered and mixed with a little ethanol to form a wet paste. A 30% w/v solution of aqueous sodium hydroxide (8 Mol. equiv.) is added and diluted with water to form a suspension/solution of the thiobenzanilide in 10% w/v aqueous sodium hydroxide. Aliquots of this suspension/solution are then introduced dropwise at one minute intervals into a stirred solution of potassium ferricyanide (4 Mol. equiv.) in water at 80–90° C. the reaction mixture is heated for a further 30 minutes, then cooled. The 2-arylbenzothiazole products are collected, washed with water and crystallised.

Where $R^2$ of the 2-arylbenzazole compound synthesised by any of the above routes (or by any other route) is a nitro group $NO_2$, this may generally be reduced and converted into the corresponding amine using Route E for which a typical procedure is as follows:

A mixture of the 2-(nitrophenyl) benzazole compound in question (0.05 Mol,) and stannous chloride dihydrate (0.25 Mol.) in absolute ethanol (200 ml) is stirred and refluxed under nitrogen for 1 to 4 hours. The ethanol is then removed under reduced pressure and the residue is dissolved in ethyl acetate (4×100 ml). The combined organic phases are next shaken with excess aqueous sodium hydroxide to liberate the free amine bases and dissolve the tin residues. The separated organic phase is washed with water, dried (magnesium sulphate) and the solvent is evaporated. Finally, the products are then crystallised.

EXAMPLES

The preparation of a number of particular compounds which are considered to be of especial interest for use as active therapeutic substances to inhibit proliferation of at least certain cancer cells and which provide example of preferred embodiments of the invention (or examples of reference compounds for comparison purposes) will now be described in more detail, together with some general procedures for specific types of reactions. The compound reference codes used elsewhere in this description are also quoted where applicable. It should be understood, however, that these specific examples are not intended to be construed in any way as limiting the scope of the invention.

Example 1

2-(4'-Aminophenyl)benzothiazole (CJM126)

A stirrable paste prepared by mixing 2-aminothiophenol (9.39 g, 0.075 mol) and 4-aminobenzoic acid (10.29 g, 0.075 mol) with PPA (120 g) was heated to 230° C. for 4 hours, cooled and poured into a large volume of 10% sodium bicarbonate solution (about 1000 ml). The solid was collected by filtration, washed with water and dried. Recrystallisation from methanol gave pale yellow needed crystals (9.65 g, 57%), m.p. 155–157° C.

Example 2

(Illustrative of General Procedure for Iodination)

2-(4'-amino-3'-iodophenyl)benzothiazole (DF129)

To a solution in acetic acid (35 ml) of 2-(4'-aminophenyl)benzothiazole (2.98 g, 0.0132 mol) prepared as above was added dropwise a solution of iodine monochloride (2.78 g, 0.0171 mol) in acetic acid (35 ml) over 10 minutes at room temperature, followed by stirring for 1½ hours. After evaporation of the solvent, 60 ml dichloromethane was added to the residue and the resulting suspension was neutralised with sodium hydrogen carbonate. Then 300 ml of water was added. The organic layer was washed with 10% sodium hydrogen carbonate solution (150 ml), water (100 ml×2) and dried (mgSO$_4$). The solvent was removed under reduced pressure, absorbed onto silica gel, and placed on top of a column of silica gel. Flash elution using ethyl acetate-hexane (2:5) yielded brown crystals (3.32 g, 69.6%), m.p. 143–144° C.

Example 3

2-(4'-amino-3'-iodophenyl)-6-methylbenzothiazole (DF219)

2-(4'-Aminophenyl)-6-methylbenzothiazole (0.6 g, 2.5 mmol) was treated with iodine monochloride (0.5 g, 3.02 mmol) in acetic acid according to the above-described general procedure for iodination. Crude product was purified by flash chromatography on silica gel, using ethyl acetate-hexane (1:3) as eluent, to give brown small crystals (0.61 g, 66.7%), m.p. 176.2–177.9° C.

Example 4

2-(4'-amino-3'-iodophenyl)-6-methoxybenzothiazole (DF210)

2-(4'-Aminophenyl)-6-methoxybenzothiazole (0.22 g, 0.84 mmol) was treated with iodine monochloride (0.21 g, 1.3 mmol) in acetic acid according to the above-described general procedure for iodination. Crude product was purified by flash chromatography on silica gel, using ethyl acetate-hexane (1:3) as eluent, to give brown small crystals (0.18 g, 54.9%), m.p. 179.2–181.1° C.

Example 5

2-(4'-amino-3'-iodophenyl)benzoxazole (DF206)

2-(4'-Aminophenyl)benzoxazole (0.14 g, 1.9 mmol) was treated with iodine monochloride (0.37 g, 2.23 mmol) in acetic acid according to the above-described general procedure for iodination. Crude product was purified by flash chromatography on silica gel using ethyl acetate-hexane (1:2) as eluent to give a brown powder (0.42 g, 65.7%), m.p. 188.0–191.2° C.

Example 6

(Illustration of General Procedure for Bromination)

2-(4'-amino-3'-bromophenyl)benzothiazole (DF209)

To a solution of 2-(4'-aminophenyl) benzothiazole (0.45 g, 1.99 mmol) in CH$_2$Cl$_2$ (50 ml) was added a solution of bromine (0.32 g, 1.99 mmol) in CH$_2$Cl$_2$ (10 ml) at –5° C. After the reaction mixture had been stirred still at –5° C. for 2 minutes, it was poured into ice-water (400 ml). The resulting mixture was stirred for 40 minutes at room temperature. The organic layer was separated, washed with 10% aqueous sodium thiosulfate (50 ml×2) and water (60 ml×2), dried (MgSO$_4$) and concentrated. The residue was chromatographed on a silica gel column, eluting with ethyl acetate-hexane (1:3), to give pale yellow crystals (0.48 g, 79.1%), m.p. 160.0–161.4° C.

Example 7

2-(4'-amino-3'-bromophenyl)-6-methylbenzothiazole (DF220)

2-(4'-Aminophenyl)-6-methylbenzothiazole (0.6 g, 2.5 mmol) was treated with bromine (0.403 g, 2.5 mmol) in dichloromethane according to the above-described general procedure for bromination. Crude product was purified by flash chromatography on silica gel, using ethyl acetate-hexane (1:3) as eluent, to give brown small crystals (0.68 g, 85.3%), m.p. 187.9–189.5° C.

Example 8

2-(4'Amino-3', 5'-dibromophenyl) benzothiazole (126)

To a solution of 2-(4'-aminophenyl)benzothiazole (0.6 g, 2,65 mmol) in 15 ml of acetic acid was added dropwise a solution of bromine (0.98 g, 6.1 mmol) in 10 ml of acetic acid at room temperature. The resulting mixture was stirred at 80° C. for 2 hours. After evaporation of acetic acid, 150 ml of 10% aqueous NaHCO$_3$ was added, followed by 150 ml of dichloromethane. The organic phase was washed with aqueous sodium thiosulphate (2×50 ml) and water (2×80 ml) and dried over MgSO$_4$. Solvent was evaporated and the residue, adsorbed onto silica gel, was chromatographed using EtOCa-hexane (1:5.5) as the eluant to give a pale yellow powder (0.7 g, 78%), mp 200.7–202.6° C.;
IR 3469, 3373, 1608, 1464, 1431, 1396, 1309, 1223, 754 cm$^{-1}$;
$\delta_H$(CLCl$_3$)8.16(s, 2H, 2',6'-H), 8.04(d, 1H, J=8.0 Hz, 4-H), 7.89(d, 1H, J=7,7 Hz, 7-H), 7.50(dt, 1H, J=1.3, 7.7 Hz, 5-H), 7.38(dt, 1H), J=1.2. 7,6 Hz, 6-H), 4.92(br s 2H, NH$_2$); $\delta_C$(CDCl$_3$) 165.8(C), 144.6(C), 135.1(C), 131.2 (2CH, C-2', 6'), 126.8 (CH), 125.6(C), 125.5(CH), 122.0 (CH), 108.9 (2C, C-3', 5'); m/z 384 (M$^+$), 305(m-Br), 224 (M+2, -Br), 196.

Example 9

2-(4'-amino-3'-chlorophenyl)benzothiazole (DF229)

A mixture of 2-(4'-amino-3'-iodophenyl) benzothiazole (0.3 g, 0.852 mmol) and copper (I) chloride (0.16 g, 10.62 mmol) in anhydrous N,N-dimethylformamide (DMF) (20 ml) under nitrogen was stirred at 155° C. for 4 hours. The reaction solution was concentrated under reduced pressure and poured into water. Product was extracted with ethyl acetate. The combined extracts were washed with water (50 ml×2), and dried (MgSO$_4$). After evaporation of solvent, the residue adsorbed onto silica gel was chromatographed, eluting with ethyl acetate-hexane (2:5), to give pale yellow crystals (0.14 g, 63%), m.p. 159.5–161.6 ° C.

Example 10

2-(4'-amino-3'-methylphenyl)benzothiazole (DF203)

A mixture of 2-aminothiophenol (2.58 g, 0.0204 mol) and 4'-amino-3'-methylbenzoic acid (3.0 g, 0.0195 mol), together with polyphosphoric acid (PPA) (60 g), was heated slowly to 210° C. The resulting solution was stirred at 210° C. for 4 hours, then permitted to cool and poured into 500 ml of 10% sodium bicarbonate solution. The precipitate formed was filtered off, washed with water, dried under reduced pressure at 50° C. The crude product was dissolved in ethyl acetate at reflux and treated with activated carbon in order to remove the deep colour. After evaporation of ethyl acetate, the product was recrystallised from methanol-water (10:3) to give pale yellow crystals (2.71 g, 58%), m.p. 193.1–195.0° C.

Example 11

2-(4'-amino-3'-ethylphenyl)benzothiazole (DF223)

A mixture of 4'-amino-3'-ethylbenzonitrile (0.9 g, 5.85 mmol) and 2-aminothiophenol (0.78 g, 6.17 mmol) in PPA (20 g) was heated to 220° C. and stirred for 4 hours. The cold resulting mixture was poured into 500 ml of 10% sodium bicarbonate solution. A black sticky solid was formed. After the water has been decanted, the black solid was treated with 5 M aqueous sodium hydroxide (40 ml) at 100° C. for 1 hour. The mixture was extracted several times with ethyl acetate. The combined organic extracts were washed with water (100 ml×2), dried (MgSO$_4$) and treated with activated carbon. Evaporation of solvent yielded a yellow solid. Recrystallisation from ethanol-water gave yellow crystals (0.45 g, 30.3%), m.p. 117.8–120.2° C.

Example 12

2-(4'-amino-3'-cyanophenyl)benzothiazole )DF230)

2-(4'-amino-3'-iodophenyl)benzothiazole (0.123 g, 0.35 mmol) was treated with copper (I) cyanide (63 mg, 0.7 mmol) in DMF according to procedure for preparation of 2-(4'-amino-3'-chlorophenyl) benzothiazole. The crude product was purified by chromatography on silica gel, eluting with ethyl acetate-hexane (2:3) to give a pale yellow powder (0.032 g, 36%%), m.p. 207.3–211.0° C.

Example 13

(Illustration of General Procedure for Acetylation)

2-(4'-Acetamidophenyl)benzothiazole (DF128)

A solution of 2-(4'-aminophenyl)benzothiazole (0.5 g, 2.21 mmol) in benzene (30 ml) and acetic anhydride (0.5 g) was stirred at reflux for 4 hours and then cooled. The white precipitate was filtered off and washed with benzene. Recrystallisation from ethyl acetate gave a white powder (0.52 g, 88%), m.p. 227.2–229.1° C.

Example 14

2-(4'-Acetamidophenyl)benzoxazole (DF140A)

2-(4'-Aminophenyl)benzoxazole (1.0 g, 4.76 mmol) was treated with acetic anhydride (5 g) in benzene according to the above-described general procedure for acetylation. A red powder was afforded (0.9 g, 75%), m.p. 213.5–214.8° C.

Example 15

2-(4'-N,N-Diacetylamino-3-methylphenyl) benzothiazole (DF212)

A 2-(4'-amino-3'-methylphenyl)benzothiazole (0.59 g, 2.46 mmol) was treated with acetic anhydride in benzene at reflux overnight. The precipitate was filtered off and washed with benzene and diethyl ether to give a white powder (0.7 g, 87.9%), m.p. 147.0–148.8° C.

Example 16

(Illustration of General Procedure for Thionation)

2-(4'-Thioacetamidophenyl)benzothiazole (DF188)

A mixture of 2-(4'-acetamidophenyl)benzothiazole (0.4 g, 1.49 mmol) and Lawesson's reagent (0.37 g, 0.9 mmol) in hexamethyl-phosphoamide (HMPA) (10 ml) was stirred at 100° C. for 6 hours. The reaction mixture was poured into water. The precipitate formed was filtered off, washed with water and dried. The crude product was purified by chromatography on silica gel, eluting with ethyl acetate-hexane (5:6)to give pale yellow crystals (0.26 g, 61%), m.p. 221.6–222.8° C.

Example 17

2-(4'-Thioacetamidophenyl)benzoxazole (DF175)

2-(4'-Acetamidophenyl)benzoxazole (0.3 g, 1.19 mmol) was treated with Lawesson's reagent (0.3 g, 0.727 mmol) in HMPA (10 ml) according to the above-described general procedure for thionation. The crude product was purified by chromatography on silica gel, eluting with ethyl acetate-hexane (2:1) to give small pale orange crystals (0.19 g, 59.5%), m.p. 211.9–213.8° C.

Example 18

2-(4'-Chloroacetamidophenyl)benzothiazole DF180)

To a solution of 2-(4'-aminophenyl)benzothiazole (0.8 g, 3.54 mmol) in benzene (40 ml) was added dropwise chloroacetylchloride (0.8 m) at 80° C. A yellow precipitate was formed and the mixture was stirred at 80° C. for 30 minutes. The precipitate was filtered, washed with benzene and diethyl ether to give a yellow powder (1.08 g, 90%), which is 2-(4'-chloroacetamidophenyl)benzothiazole hydrochloride.

A fine powder of the above salt (0.8 g) was treated with 10% aqueous Na$_2$CO$_3$ (40 ml) at 50° C. for 1 hour. The product was filtered, washed with water and dried to afford a pale yellow powder (0.63 g, 88), m.p. 214.2–215.4° C.

Example 19

2-(4'-Chloroacetamidophenyl)benzoxazole (DF190)

2-(4'-Aminophenyl)benzoxazole (0.28 g, 1.33 mmol) was treated with chloroacetyl chloride (0.5 ml) in benzene (15 ml) according to the procedure described above for preparation of 2-(4'-chloroacetamidophenyl)benzothiazole. 2-(4'-Chloroacetamidophenyl)benzoxazole hydrochloride was obtained (0.31 g, 72%).

A suspension of the salt (0.228 g) in 10% aqueous $Na_2CO_3$ (10 ml) was stirred at 50° C. for 1 hour. The solid was filtered, washed with water and dried. The product was chromatographed, using ethyl acetate-hexane (1:2) as eluent, to give white crystals (0.18 g, 89%), m.p. 200.0–201.8° C.

Example 20

2-(4'- Chloroacetamido-3-iodophenyl) benzothiazole (DF225)

To a solution of 2-(4'-amino-3'-iodophenyl) benzothiazole (DF129) (0.15 g, 0.426 mmol) in benzene (15 ml) was added dropwise chloroacetyl chloride (0.18 g) at room temperature. A yellow precipitate was formed and the resulting mixture was stirred at 50° C. for 30 minutes, and then cooled in an ice-bath. The solid was filtered off, washed with cold benzene and petroleum ether, and dried to give a yellow powder (0.13 g, 71.2%), m.p. 192.1–193.8° C.

Example 21

2-(4'-Acetamide-3-nitrophenyl)benzothiazole (DF214)

A solution of 2-(4'-aminophenyl)benzothiazole (0.356 g, 1.57 mmol) in acetic anhydride (25 ml) and benzene (15 ml) was treated with copper (II) nitrate hydrate (0.31 g) and the mixture stirred at room temperature overnight. Subsequent evaporation of the mixture under reduced pressure gave a residue which was suspended in ethyl acetate (150 ml) and neutralised with 10% aqueous sodium bicarbonate (50 ml). After addition of water (100 ml) the organic layer was separated, washed with water (80 ml×2) and dried ($MgSO_4$). The solvent was evaporated onto silica gel, which was chromatographed, using ethyl acetate-hexane (1:3, 1:1) as eluent, to give a brown powder (0.16 g, 32.5%), m.p. 232.4–234.2° C.

Example 22

2-(4'-Dichloroacetamidophenyl) benzothiazole (DF232)

To a solution of 2(4'-aminophenyl)benzothiazole (0.4 g, 1.77 mmol) in benzene (20 ml) was added dropwise dichloroacetyl chloride (0.34 ml) at 80° C. The yellow precipitate was formed and the mixture was stirred at 80° C. for 30 minutes. The precipitate was filtered off, washed with benzene and diethyl ether to give (2-(4'-dichloroacetamidophenyl) benzothiazole hydrochloride as a yellow powder (0.56 g, 84,8%). A fine powder of the above salt (0.25 g) was treated with 10% aqueous $Na_2CO_3$ (15 ml) for 50° C. for 1 hour, the product was collected by filtration, washed with water and dried to afford a white powder (0.2 g, 88.6%), m.p. 223.0–225.2° C.

Example 23

2-(4'-Benzamidophenyl)benzothiazole (DF131)

This is an example of a benzoyl derivative.

A mixture of 2-(4'-aminophenyl)benzothiazole (0.3 g, 1.32 mmol) and benzoyl chloride (0.3 ml) in pyridine (8 ml) was stirred at reflux for 2 hours, then cooled and poured into water (100 ml). The precipitate formed was filtered off, washed with water and dissolved in hot dichloromethane (12 ml). The resulting solution was cooled in an ice-bath and the solid was filtered off. The filtrate was evaporated and the residue was recrystallised from dichloromethane-methanol to give a white powder (0.36 g, 82.2%), m.p. 227.1–228.5° C.

Example 24

2-(4'-Cyclobutamidophenyl)benzothiazole (KF497)

This is an example of a cyclic amide derivative.

To a solution of 2-(4'-aminophenyl)benzothiazole (0.8 g, 3.54 mmol) in benzene (40 ml) at 80° C. was added dropwise cyclobutanecarbonyl chloride (1.1 ml, 9.64 mmol). A yellow solid formed, and the mixture was stirred at 80° C. for 30 minutes. The solid was filtered, washed with benzene and diethyl ether to give a yellow powder (1.18 g, 96.9%), which is a 2-(4'-cyclobutylacetamidophenyl) benzothiazole hydrochloride, m.p. 247–248° C.

A fine powder of the above salt (1.0 g, 2.91 mmol) was treated with aqueous ammonia (s.g.=0.88) at 50° C. for 1 hour. The product was filtered, washed with water and dried to afford a pale yellow powder (0.81 g, 90.3%).

This was recrystallised from ethanol to give a white solid (0.61 g, 70%), m.p. 248–249° C.
$^1$H NMR ($\delta$,ppm)
10.09 (1H, S, —NH); 8.12 (1H, d, Ar 4-H);
8.05 (2H, d, Ar 2 ',6'-H); 8.03 (1H, d Ar 7-H);
7.83 (2H, d Ar 3',5'-H); 7.53 (1H, t, Ar 5-H);
7.44 (1H, t, Ar 6-H); 3.29(1H, quint 1"-H);
2.01-1.80 (6H, m 2", 3", 4"-H)

Example 25

(Illustration of General Procedure for Preparation of Sulphamate Salts)

Sodium 4-(benzothiazol-2-yl)phenylsulphamate (DF183)

To anhydrous 2-picoline (1.05 g, 11 mmol) was slowly added dropwise chlorsulphonic acid (0.26 g, 2.21 mmol) below 10° C. then 2-(4'-amino-3'-iodophenyl)benzothiazole (0.5 g, 2.21 mmol). The mixture was heated to 50° C. with stirring for 1 hour. After leaving to stand for 2 hours at room temperature, 6 ml of 10% aqueous sodium carbonate was added. The resulting mixture was stirred for 40 minutes at room temperature and concentrated under reduced pressure. The precipitate was filtered off, washed carefully with cold water and treated with hot chlorform. Golden crystals were afforded (0.62 g, 85.5%), m.p. 288–290° C.

Example 26

Ammonium 4-(benzothiazol-2-yl)phenylsulphamate (DF191)

2(4'-Aminophenyl)benzothiazole was treated with chlorsulphonic acid in 2-picoline according to the above-described general procedure for preparation of sulphamate salts. About 35% ammonia solution instead of 10% aqueous $Na_2CO_3$ was used. A yellow powder was afforded in 69% yield, m.p. 223.1–226.8° C.

Example 27

Sodium 4-(benzoxazol-2-yl)phenylsulphamate (DF187)

2(4'-Aminophenyl)benzoxazole was treated with chlorsulphonic acid in 2-picoline and sodium carbonate according to the above-described general procedure for preparation of sulphamate salts. Grey crystals were obtained in 96% yield, m.p. >340° C.

Example 28

Sodium 4-(benzothiazol-2yl)-3-iodopheynlsulphamate (DF224)

2-(4'-amino-3'-iodophenyl)benzothiazole was treated with chlorsulphonic acid in 2-picoline and sodium carbonate according to the above-described general procedure for preparation of sulphamate salts. A white powder was obtained in 79% yield, m.p. >340° C.

Example 29

Sodium 4-(benzothiazol-2-yl)-3-methylphenylsulphamate (DF228)

2-(4'-amino-3'-methylphenyl)benzothiazole was treated with chlorsulphonic acid in 2-picoline and sodium carbonate according to the above-described general procedure for preparation of sulphamate salts. A yellow powder was obtained in 82% yield, m.p. 169.5° C. (dec).

Therapeutic Use

As already indicated, compounds of this invention have been found to inhibit tumor cell proliferation and to have significant selective antitumor activity. Antitumor activity may be evidenced by reduction of tumor cell number in mammals bearing cancer tumors, e.g. breast cancer tumors, and a consequent increase in survival time as compared to a control provided by animals which are untreated. Antitumor activity is further evidenced by measurable reduction in the size of solid tumors following treatment with the compounds of this invention compared to the tumors of untreated control animals.

Accordingly, as previously stated the compounds of the present invention are of particular interest for the treatment of a range of selected cancer tumors, and the invention further provides a method for the treatment of a patient suffering from certain kinds of cancer. For this purpose, an effective non-toxic amount of the active 2-arylbenzazole compound, or an acid addition salt or sulphamate salt, or close analogue thereof (including for example an acyl or benzoyl derivative) as hereinbefore defined, may be suitably administered, orally, parenterally (including subcutaneously, intramuscularly and intravenously), or topically. The administration will generally be carried out repetitively at intervals, for example once or several times a day.

The amount of the benzazole compound which is required in order to be effective as an antitumor agent for treating mammals will of course vary and is ultimately at the discretion of the medical or veterinary practitioner treating the mammal in each particular case. The factors to be considered by such practitioner, e.g. a physician, include the route of administration and pharmaceutical formulation; the mammal's body weight, surface area, age and general condition; and the chemical form of the compound to be administered. However, a suitable effective antitumor dose may be in the range of about 1.0 to about 75 mg/kg bodyweight, preferably in the range of about 5 to 40 mg/kg with most suitable doses being for example in the range of 10 to 30 mg/kg. In daily treatment for example, the total daily dose may be given as a single dose, multiple doses, e.g. two to six times per day, or by intravenous infusion for any selected duration. For example, in the case of a 75 kg mammal, the dose range could be about 75 to 500 mg per day, and it is expected that a typical dose would commonly be about 100 mg per day. If discrete multiple doses are indicated, treatment might typically be 50 mg of the arylbenzazole compound as hereinbefore defined, given 4 times per day in the form of a table, capsule, liquid (e.g. syrup) or injection. On account of a biphasic dose response characteristics of some of these compound, however, care should be taken, particularly in the initial stages of treatment, to ensure that dosage amounts are not too high.

While it may be possible for the benzazole compounds of this invention to be administered alone as the raw chemical, it is preferable to present the compounds as a pharmaceutical formulation. Formulations of the present invention, for medical use, will generally comprise the active compound or a prodrug form thereof together with one or more pharmaceutically acceptable carriers and optionally, any other therapeutic ingredients. The carrier(s) must be pharmaceutically acceptable in the sense of being compatible with the other ingredients of the formulation and not deleterious to the recipient thereof.

The present invention therefore further provides a pharmaceutical formulation comprising an arylbenzazole compound as hereinbefore specified (possibly in the form of a free base or a pharmaceutically acceptable acid addition salt) together with a pharmaceutically acceptable carrier thereof.

The possible formulations include those suitable for oral, rectal, topical and parenteral (including sub-cutaneous, intramuscular and intravenous) administration.

The formulations may conveniently be presented in unit dosage form and may be prepared by any of the methods well known in the art of pharmacy. All methods include generally the step of bringing the active compound into association with a carrier which constitutes one or more accessory ingredients. Usually, the formulations are prepared by uniformly and intimately bringing the active compound into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallisation of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parental administration conveniently comprise a sterile aqueous preparation of the active compound which is preferably isotonic with the blood of the recipient.

In addition to the aforementioned ingredients, formulations of this invention, for example ointments, creams and the like, may include one or more accessory ingredient(s) selected from diluents, buffers, flavouring agents, binders, surface active agents, thickeners, lubricants, preservatives (including antioxidants) and the like.

From another aspect, the invention thus also comprises use of a benzazole compound as hereinbefore specified for the manufacture of a medical preparation for cancer treatment.

TABLE 1

In vitro inhibitory activity of benzothiazoles against human lung cancer cell lines

| COMPOUND | | | | |
|---|---|---|---|---|
| Number | R | $R^1$ | CELL LINE | $IC_{50}$ ($\mu$M)* |
| CJM 126 | $NH_2$ | H | H69/P | >10 |
| | | | LX4 | >10 |
| | | | L23/P | >10 |
| | | | L23/R | >10 |
| | | | MOR/P | >10 |
| | | | MOR/R | >10 |
| DF129 | $NH_2$ | I | H69/P | >10 |
| | | | LX4 | >10 |
| | | | L23/P | 0.1 |
| | | | L23/R | >10 |
| | | | MOR/P | 0.3 |
| | | | MOR/R | 0.1 |
| | | | MOR/CPR | 0.025 |
| | | | L88 | 0.05 |
| | | | NCI HOP-92 | <0.01 |
| | | | NCI-H226 | 0.3 |
| DF180 | $NHCOCH_2CL$ | H | H69/P | 3 |
| | | | LX4 | 3 |
| | | | L23/P | 1.5 |
| | | | L23/R | 1.5 |
| | | | MOR/P | 6 |
| | | | MOR/R | 6 |
| | | | MOR/CPR | 10 |
| | | | L88 | 6 |
| DF203 | $NH_2$ | Me | H69/P | >10 |
| | | | LX4 | >10 |
| | | | L23/P | 10 |
| | | | L23/R | >10 |
| | | | MOR/P | 0.1 |
| | | | MOR/R | 0.07 |
| | | | MOR/CPR | 0.04 |
| | | | L88 | 6 |
| | | | NCI-H226 | 0.3 |

*Concentration which causes 50% inhibition of cell growth

TABLE 2

In vitro activity of benzothiazoles against human ovarian cell lines

| COMPOUND | | | | |
|---|---|---|---|---|
| Number | R | $R^1$ | CELL LINE | $IC_{50}$ ($\mu$M) |
| DF129 | $NH_2$ | I | IGR-OV1 | <0.1 |
| | | | OVCAR-3 | 0.6 |
| | | | OVCAR-4 | 0.2 |
| | | | OVCAR-5 | 0.3 |
| | | | OVCAR-8 | >100 |
| | | | SK-OV-3 | >100 |
| | | | A2780 | >100 |
| | | | A2780-cisR | 41 |
| | | | CH1 | 30 |
| | | | CH1-cisR | 83 |
| DF180 | $NHCOCH_2CL$ | H | A2780 | 1.25 |
| | | | A2780-cisR | 1.6 |
| | | | CH1 | 1.6 |
| | | | CH1-cisR | 2.6 |
| DF203 | $NH_2$ | Me | ICR-OV1 | <0.1 |
| | | | OVCAR-3 | not tested |
| | | | OVCAR-4 | <1 |
| | | | OVCAR-5 | not tested |
| | | | OVCAR-8 | >100 |
| | | | SK-OV-3 | >100 |
| | | | A2780 | >100 |
| | | | A2780-cisR | 18 |
| | | | CH1 | 19 |
| | | | CH1-cisR | 42 |
| Cisplatin (reference) | | | A2780 | 0.33 |
| | | | A2780-cisR | 5.2 |
| | | | CH1 | 0.1 |
| | | | CH1-cisR | 0.7 |

TABLE 3

In vitro inhibitory activity of benzothiazoles against human colon, renal and prostatic cell lines

| COMPOUND | | | | |
|---|---|---|---|---|
| Number | R | $R^1$ | CELL LINE | $IC_{50}$ ($\mu$M) |
| DF129 | $NH_2$ | I | Colon HCC-2998 | <1 |
| | | | Colon SW-620 | ~100 |
| | | | Renal TK-10 | <1 |
| | | | Renal ACHN | >100 |
| | | | Prostatic PC3 MAZ | 54 |
| | | | Prostatic DU 145 | 52 |
| DF203 | $NH_2$ | Me | Colon HCC-2998 | <1 |
| | | | Colon SW-620 | >100 |
| | | | Renal TK-10 | <1 |
| | | | Renal ACHN | ~100 |
| | | | Prostatic PC3 MAZ | >100 |
| | | | Prostatic DU 145 | >100 |

TABLE 4

In vitro inhibitory activity of benzothiazoles
against human breast tumour cell lines

| | COMPOUND | | | $IC_{50}$ |
|---|---|---|---|---|
| Number | R | $R^1$ | CELL LINE* | (μM) |
| DF129 | $NH_2$ | I | MCF-7wt | <1 nM |
| | | | MDA 468 | <1 nM |
| | | | SDBR3 | <1 nM |
| DF180 | $NHCOCH_2CL$ | H | MCF-7wt | 0.004 μM |
| | | | MDA 468 | 0.04 μM |
| | | | MCF-7B | 0.5 μM |
| DF203 | $NH_2$ | Me | MCF-7wt | <1 nM |
| | | | MDA 468 | <1 nM |
| | | | MCF-7B | 0.01 μM |
| DF209 | $NH_2$ | Br | MCF-7wt | <1 nM |
| | | | MDA 468 | <1 nM |
| | | | MCF-7B | 0.001 μM |

*Initial seeding density $2.5 \times 10^2$ cells/well

TABLE 5

| Compound | Tumor | Schedule | dose[a] (mg/Kg/inj.) | BWC[b] (%) | TRV[c] (T/C %) | evaluation[d] |
|---|---|---|---|---|---|---|
| CJM 126 | BO | qd 27, 34, 41 | 100 | −7 | 52* | (+) |
| | | qd 27, 34, 41 | 10 | −4 | 52* | (+) |
| | | qd 27, 34, 41 | 1 | −5 | 41* | + |
| 2-(3-Aminophenyl)-benzothiazole | BO | qd 27, 34, 41 | 200 | −6 | 32* | ++ |
| | | qd 27, 34, 41 | 20 | −3 | 48* | + |
| | | qd 27, 34, 41 | 2 | 2 | 78 | − |

[a]By i.p. route.
[b]Body weight change.
[c]Relative tumor volume.
[d](+), T/C % ≥ 51%; +, T/C % = 36–50%; ++, T/C = 21–35%.
*Significant versus controls (p < 0.05)

TABLE 6

| Compound | Tumor[a] | Optimum dose[b] (mg/Kg/inj) | Schedule | WBC[c] (% of controls) | Platelets | BWC[d] (%) | RTV[e] (T/C %) | Evaluation[f] |
|---|---|---|---|---|---|---|---|---|
| DF 203 | BO | 25 | qd 27, 34, 41 | n.t. | n.t. | −9 | 35* | ++ |
| | MCF-7 | 12.5 | qd 12, 19, 26 | 100 | 108 | −12 | 31* | ++ |
| | MT-1 | 6.25 | qd 7, 14, 21 | n.t. | n.t. | −3 | 34* | ++ |
| | MT-3 | 12.5 | qd 7, 14, 21 | n.t. | n.t. | −3 | 22* | ++ |
| DF 129 | BO | 200 | qd 27, 34, 41 | n.t. | n.t. | −14 | 97 | − |
| | MCF-7 | 200 | qd 12, 19, 26 | 112 | 106 | −14 | 68* | (+) |

[a]Implanted s.c.
[b]By i.p. route.
[c]White blood cells.
[d]Body weight change.
[e]Relative tumor volume.
[f]See footnote d, Table 5,
n.t. Not tested.
*Significant versus control (p > 0.05).

We claim:
1. A pharmaceutical composition suitable for administration to a mammal and comprising an effective amount of a benzazole compound of structural formula I below, or a pharmaceutically acceptable salt thereof,

I wherein:
X is S or O,
$R^1$ and $R^3$ are each independently hydrogen, alkyl, hydroxyl, alkoxy or aralkoxy,
$R^2$ is selected from hydrogen, $NO_2$, $NH_2$, halogen, alkyl, CN, and a substituted alkyl oxysulphonyl group;
$R^5$ and $R^6$ are each independently hydrogen, alkyl, benzoyl or an acyl group $$-\underset{\underset{R^8}{|}}{C}=Y$$

where Y is O or S, and $R^8$ is alkyl, or halogenated alkyl, or $SO_3^-M^+$ where $M^+$ is a monovalent cation or cationic group; and $R^7$ is hydrogen, 5'-halogen or 5'-alkyl, together with a pharmaceutically acceptable carrier therefor, subject to the following provisos:
  a) when $R^5$ and $R^6$ are each hydrogen or alkyl, $R^2$ is not hydrogen but is a 3'-substituent in the phenyl group other than a 3'-substituted alkyl oxysulphonyl group;
  b) $R^7$ is limited to being hydrogen unless $R^2$ is a 3'-substituent in the phenyl group;
  c) if $R^2$ is $NO_2$ it is a 3'-substituent in the phenyl group;
  d) alkyl groups are each composed of less than 6 carbon atoms;
  e) the compound is not 2-(4'-amino-3'-iodophenyl) benzothiazole or a salt thereof other than a sulphamate salt;
  f) $R^8$ is not alkyl or cycloalkyl when $R^2$ is hydrogen, said pharmaceutical composition being in cachet, tablet, capsule, lozenge suppository, syrup or elixir form, or being in the form of a sterile liquid formulation, a paste or electuary, a powder or granules or an ointment or cream.

2. A pharmaceutical composition as claimed in claim 1 comprising at least one of the following features:
  (a) at least some alkyl groups are methyl or ethyl;
  (b) halogen substituents are selected from the group consisting of iodine, bromine and chlorine.

3. A pharmaceutical composition as claimed in claim 1 wherein $R^2$ is a substituent in the 3'position of the phenyl group.

4. A pharmaceutical composition as claimed in claim 3 wherein $R^1$ is selected from an alkyl, alkoxy or benzyloxy substituent in the 6 position of the benzazole moiety.

5. A pharmaceutical composition as claim 1 wherein $R^3$ is hydrogen, $R^1$ is selected from alkyl, alkoxy or benzyloxy, and X is sulphur.

6. A pharmaceutical composition as claimed in claim 5 wherein $R^2$ is selected from 3'-I, 3'-Br and 3'-Cl.

7. A pharmaceutical composition as claimed in claim 6 wherein $R^1$ is 6-Me or 6-OMe.

8. A pharmaceutical composition as claimed in claim 1 wherein $R^2$ is 3'-Me or 3'-OMe.

9. A pharmaceutical composition as claimed in claim 1 wherein $R^5$ and $R^6$ are both hydrogen and the combination of substituents $R^1$, $R^2$, $R^3$, $R^7$ and X is selected from the group made up of following combinations:

| $R^1$ | $R^3$ | X | $R^2$ | $R^7$ |
|---|---|---|---|---|
| H | H | S | 3'-Me | H |
| H | H | S | 3'-Et | H |
| 6-Me | H | S | 3'-I | H |
| 6-OMe | H | S | 3'-I | H |
| H | H | O | 3'-I | H |
| H | H | S | 3'-Br | H |
| 6-Me | H | S | 3'-Br | H |
| H | H | S | 3'-Cl | H |
| H | H | S | 3'-CN | H |
| H | H | S | 3'-Br | 5'-Br |
| H | H | S | 3'-Cl | 5'-Cl |
| H | H | S | 3'-Cl | 5'-Me. |

10. A pharmaceutical composition as claimed in claim 1 wherein $R^1$ and $R^3$ are both hydrogen and the substituent $NR^5R^6$ is represented by the structural formula:

wherein Y is O or S and $R^8$ is selected from the group consisting of alkyl or cycloalkyl, a halogenated alkyl, and phenyl, subject to the proviso that $R^8$ is not alkyl or cycloalkyl when $R^2$ is hydrogen.

11. A pharmaceutical composition as claimed in claim 10 wherein the substituent $NR^5R^6$ is an N-acyl group and the combination of substituents $R^2$, $R^8$, X and Y is selected from the group consisting of following combinations:

| X | $R^2$ | Y | $R^8$ |
|---|---|---|---|
| S | H | S | Me |
| O | H | S | Me |
| S | H | O | $CH_2Cl$ |
| O | H | O | $CH_2Cl$ |
| O | 3'-I | O | $CH_2Cl$ |
| O | 3'-$NO_2$ | O | Me |
| S | H | O | $CHCl_2$ |
| S | H | O | Ph. |

12. A pharmaceutical composition as claimed in claim 1 wherein said benzazole compound is an acid addition salt derived from an acid selected from the group consisting of hydrochloric, hydrobromic, sulphuric, nitric, phosphoric, maleic, salicyclic, p-toluenesulphonic, tartaric, citric, lactobionic, formic, malonic, pantothenic, succinic, naphthalene-2-sulphonic, benzenesulphonic, methanesulphonic and ethanesulphonic.

13. A pharmaceutical composition as claimed in claim 1 wherein the benzoxazole is a sulphamate salt in which the substituent $NR^5R^6$ is $NHSO_3^-M^+$, $M^+$ being a cation.

14. A pharmaceutical composition as claimed in claim 13 wherein the combination of substituents $R^1$, $R^2$, $R^3$, $NR^5R^6$ and X is selected from the group consisting of the following combinations:

| $R^1$ | $R^3$ | X | $R^2$ | $NR^5R^6$ |
|---|---|---|---|---|
| H | H | S | H | $NHSO_3^-Na^+$ |
| H | H | S | H | $NHSO_3^-NH_4^+$ |
| H | H | O | H | $NHSO_3^-Na^+$ |
| H | H | S | 3-I | $NHSO_3^-Na^+$ |
| H | H | S | 3-Me | $NHSO_3^-Na^+$. |

15. A pharmaceutical composition as claimed in claim 1 in unit dosage form suitable for oral, rectal or parenteral administration.

16. A pharmaceutical composition as claimed in claim 15 in cachet, tablet, capsule or lozenge form.

17. A pharmaceutical composition comprising an effective amount of a benzazole compound which is selected from the group consisting of the following:

2-(4'-amino-3'-iodophenyl)-6-methylbenzothiazole 2-(4'-amino-3'-iodophenyl)-6-methoxybenzothiazole

2-(4'-amino-3'-iodophenyl)benzoxazole 2-(4'-amino-3'-bromophenyl)benzothiazole 2-(4'-amino-3'-bromophenyl)-6-methylbenzothiazole

2-(4'amino-3',5'-dibromophenyl)benzothiazole
2-(4'-amino-3'-chlorophenyl)benzothiazole
2-(4'-amino-3'-methylphenyl)benzothiazole
2-(4'-amino-3'-ethylphenyl)benzothiazole
2-(4'-amino-3'-cyanophenyl)benzothiazole
2-(4'-N,N-Diacetylamino-3-methylphenyl)benzothiazole
2-(4'-Thioacetamidophenyl)benzothiazole
2-(4'-Thioacetamidophenyl)benzoxazole
2-(4'-Chloroacetamidophenyl)benzothiazole
2-(4'-Chloroacetamidophenyl)benzoxazole
2-(4'-Chloroacetamido-3'-iodophenyl)benzothiazole
2-(4'-Acetamido-3'-nitrophenyl)benzothiazole
2-(4'-Dichloroacetamidophenyl)benzothiazole
2-(4'-Benzamidophenyl)benzothiazole
Sodium 4'-(benzothiazole2-yl)phenylsulphamate
Ammonium 4'-(benzothiazole-2-yl)phenylsulphamate
Sodium 4'-(benzoxazole-2-yl)phenylsulphamate
Sodium 4'-(benzothiazol-2-yl)-3'-iodophenylsulphamate
Sodium 4'-(benzothiazole-2-yl)-3'-methylphenylsulphamate, said pharmaceutical composition being in cachet, table, capsule, lozenge, suppository, syrup or elixir form, or being in the form of a sterile liquid formulation, a paste or electuary, a powder or granules or an ointment or cream.

18. A pharmaceutical composition suitable for administration to a mammal and comprising an effective amount of a banzazole compound of structural formula I below, or a pharmaceutically acceptable salt thereof,

I wherein
X is S;
$R^1$ is alkyl, alkoxy or benzyloxy;
$R^2$ is 3'-I, 3'-Br or 3'-Cl;
$R^3$ is hydrogen;
$R^5$ and $R^6$ are each independently hydrogen, alkyl, benzoyl or an acyl group where Y is O or S, and
$R^8$ is alkyl, cycloalkyl or halogenated alkyl, or $SO_3^-M^+$ where $M^+$ is a monovalent cation or cationic group; and
$R^7$ is hydrogen, 5'-halogen or 5'-alkyl, together with a pharmaceutically acceptable carrier therefor.

19. A pharmaceutical composition as claimed in claim 18 wherein $R^1$ is 6-Me or 6-OMe.

20. A pharmaceutical composition in unit dosage form selected from cachet, tablet, capsule or lozenge form comprising a benzazole compound admixed with a pharmaceutically acceptable carrier therefor, said benzazole compound being represented by the structural formula I below, or a pharmaceutically acceptable salt thereof:

I wherein:
X is S or O;
$R^1$ and $R^3$ are each independently hydrogen, alkyl, hydroxyl, alkoxy or aralkoxy;
$R^2$ is selected from hydrogen, $NO_2$, $NH_2$, halogen, alkyl, CN, and a substituted alkyl oxysulphonyl group;
$R^5$ and $R^6$ are each independently hydrogen, alkyl, or $SO_3^-M^+$ where M' is a monovalent cation or cationic group; and
$R^7$ is hydrogen, 5'-halogen or 5-alkyl, subject to the following provisos:
(a) when $R^5$ and $R^6$ are each hydrogen or alkyl, $R^2$ is not hydrogen but is a 3'-substituent in the phenyl group other than a 3'-substituted alkyl oxysulphonyl group;
(b) $R^7$ is limited to being hydrogen unless $R^2$ is a 3'-substituent in the phenyl group;
(c) if $R^2$ is $NO_2$ it is a 3'-substituent in the phenyl group;
(d) alkyl groups as alkoxy are each composed of less than 6 carbon atoms;
(e) the compound is not 2-(4'-amino-3'-iodophenyl) benzothiazole or a salt thereof other than a sulphamate salt thereof);
(f) the compound is not 2-(4'amino-3',5'-dibromophenyl)benzothiazole; and
(g) neither $R^5$ and $R^6$ is an acyl or benzoyl group.

21. A medical preparation in unit dosage form selected from cachet, tablet, capsule or lozenge form containing a therapeutically effective non-toxic amount of a benzazole compound and a pharmaceutically inert excipient, said benzazole compound being represented by the structural formula I below, or a pharmaceutically acceptable salt thereof:

I wherein:
X is S or O;
$R^1$ and $R^3$ are each independently hydrogen, alkyl, hydroxyl, alkoxy or aralkoxy;
$R^2$ is selected from hydrogen, $NO_2$, $NH_2$, halogen, alkyl, CN, and a substituted alkyl oxysulphonyl group;
$R^5$ and $R^6$ are each independently hydrogen, alkyl, or $SO_3^-M^+$ where M' is a monovalent cation or cationic group; and
$R^7$ is hydrogen, 5'-halogen or 5-alkyl, subject to the following provisos:
(a) when $R^5$ and $R^6$ are each hydrogen or alkyl, $R^2$ is not hydrogen but is a 3'-substituent in the phenyl group other than a 3'-substituted alkyl oxysulphonyl group;

(b) R⁷ is limited to being hydrogen unless R² is a 3'-substituent in the phenyl group;
(c) if R² is NO₂ it is a 3'-substituent in the phenyl group;
(d) alkyl groups as alkoxy are each composed of less than 6 carbon atoms;
(e) the compound is not 2-(4'-amino-3'-iodophenyl) benzothiazole or a salt thereof other than a sulphamate salt thereof);
(f) the compound is not 2-(4'amino-3',5'-dibromophenyl)benzothiazole; and
(g) neither R⁵ nor R⁶ is an acyl or benzoyl group.

22. A pharmaceutical preparation in unit dosage form selected from cachet, tablet, capsule or lozenge form for administering to a mammal to obtain a therapeutic effect as an antitumor agent, said preparation comprising, per-dosage unit, a therapeutically-effective amount of a benzazole compound together with a pharmaceutically acceptable carrier, said benzazole being selected from the group consisting of the following:

2-(4'-amino-3'-iodophenyl)-6-methylbenzothiazole
2-(4'-amino-3'-iodophenyl)-6-methoxybenzothiazole
2-(4'-amino-3'-iodophenyl)benzoxazole
2-(4'-amino-3'-bromophenyl)benzothiazole
2-(4'-amino-3'-bromophenyl)-6-methylbenzothiazole
2-(4'amino-3',5'-dibromophenyl)benzothiazole
2-(4'-amino-3'-chlorophenyl)benzothiazole
2-(4'-amino-3'-methylphenyl)benzothiazole
2-(4'-amino-3'-ethylphenyl)benzothiazole
2-(4'-amino-3'-cyanophenyl)benzothiazole
2-(4'-N,N-Diacetylamino-3-methylphenyl)benzothiazole
2-(4'-Thioacetamidophenyl)benzothiazole
2-(4'-Thioacetamidophenyl)benzoxazole
2-(4'-Chloroacetamidophenyl)benzothiazole
2-(4'-Chloroacetamidophenyl)benzoxazole
2-(4'-Chloroacetamido-3'-iodophenyl)benzothiazole
2-(4'-Acetamido-3'-nitrophenyl)benzothiazole
2-(4'-Dichloroacetamidophenyl)benzothiazole
2-(4'-Benzamidophenyl)benzothiazole
Sodium 4'-(benzothiazol-2-yl)phenylsulphamate
Ammonium 4'-(benzothiazole-2-yl)phenylsulphamate
Sodium 4'-(benzoxazole-2-yl)phenylsulphamate
Sodium 4'-(benzothiazole-2-yl)-3'-iodophenylsulphamate
Sodium 4'-(benzothiazole-2-yl)-3'-methylphenylsulphamate.

23. A method of treating a mammal suffering from cancer so as to inhibit or reduce cancer cell growth, said method comprising administering to said mammal an effective antitumor composition as defined in claim 1.

24. A method of treating a mammal suffering from cancer so as to inhibit or reduce can cancer cell growth, said method comprising administering to said mammal an effective amount of a compound of formula I or a pharmaceutically acceptable salt thereof:

I wherein
X is S or O;
R¹ and R³ are each independently hydrogen, alkyl, hydroxyl, alkoxy or aralkoxy;
R² is selected from hydrogen, NO₂, NH₂, halogen, alkyl, CN, and a substituted alkyl oxysulphonyl group;
R⁵ and R⁶ are each independently hydrogen, alkyl, benzoyl or an acyl group where Y is O or S, and
R⁸ is alkyl, cycloalkyl or halogenated alkyl, or SO₃⁻M⁺ where M⁺ is a monovalent cation or cationic group; and
R⁷ is hydrogen, 5'-halogen or 5'-alkyl, subject to the following provisos:
(a) when R⁵ and R⁶ are each hydrogen or alkyl, R² is not hydrogen but is a 3'-substituent in the phenyl group other than a 3'-substituted alkyl oxysulphonyl group;
(b) R⁷ is limited to being hydrogen unless R² is a 3'-substituent in the phenyl group;
(c) if R² is NO₂ it is a 3'-substituent in the phenyl group;
(d) alkyl groups when present as such in the compound or as a moiety in other groups such as alkoxy are each composed of less than 6 carbon atoms;
(e) the compound is not 2-(4'-amino-3'-iodophenyl) benzothiazole or salt thereof other than sulphamate salt thereof.

* * * * *